(12) United States Patent
Dubey et al.

(10) Patent No.: US 12,158,467 B2
(45) Date of Patent: Dec. 3, 2024

(54) METHOD FOR TESTING OF ANTIBIOTIC SUSCEPTIBILITY IN MICROORGANISMS

(71) Applicant: MODULE INNOVATIONS PRIVATE LIMITED, Pune (IN)

(72) Inventors: Sachin Dubey, Pune (IN); Usman Khan, Pune (IN); Rahul Chaudhari, Pune (IN); Maya Kv, Pune (IN)

( * ) Notice: Subject to any disclaimer, the term of this patent is extended or adjusted under 35 U.S.C. 154(b) by 991 days.

(21) Appl. No.: 17/261,202

(22) PCT Filed: Nov. 26, 2019

(86) PCT No.: PCT/IB2019/060153
§ 371 (c)(1),
(2) Date: Jan. 19, 2021

(87) PCT Pub. No.: WO2020/109986
PCT Pub. Date: Jun. 4, 2020

(65) Prior Publication Data
US 2021/0278402 A1   Sep. 9, 2021

(30) Foreign Application Priority Data
Nov. 27, 2018   (IN) .............................. 201821044730

(51) Int. Cl.
*G01N 33/553*   (2006.01)
*G01N 33/53*   (2006.01)

(52) U.S. Cl.
CPC ....... *G01N 33/553* (2013.01); *G01N 33/5308* (2013.01); *G01N 2333/904* (2013.01)

(58) Field of Classification Search
CPC .................................................. G01N 33/553
See application file for complete search history.

(56) References Cited

U.S. PATENT DOCUMENTS

| 2015/0064703 A1 | 3/2015 | Super et al. |
| 2015/0330976 A1 | 11/2015 | Chen et al. |

FOREIGN PATENT DOCUMENTS

| CN | 104990913 A | 10/2015 |
| CN | 108627559 A | 10/2018 |
| IN | 3229MUM2010 | 6/2013 |
| WO | 2013130875 A1 | 9/2013 |
| WO | 2017106425 A1 | 6/2017 |
| WO | 2018144431 A1 | 8/2018 |

OTHER PUBLICATIONS

Kaittanis C, Nath S, Perez JM. Rapid nanoparticle mediated monitoring of bacterial metabolic activity and assessment of antimicrobial susceptibility in blood with magnetic relaxation. PLoS One. Sep. 23, 2008;3(9):e3253.

Zhang H et al: "A novel glucose biosensor based on direct electrochemistry of glucose oxidase incorporated in biomediated gold nanoparticles-carbon nanotubes composite film", Sensors and Actuators B: Chemical, 2011, vol. 158, No. 1, pp. 23-27, whole document.

*Primary Examiner* — Albert M Navarro

(57) ABSTRACT

The present invention relates to novel diagnostic tools including system, method and kit for determining antibiotic susceptibility in microorganisms directly in a clinical sample. Specifically, the present invention relates to a diagnostic system and method for testing antibiotic susceptibility based on a phenotypic screening of the microorganisms in the presence of major antibiotics being used currently. The present invention can be used directly on the clinical samples and obliterates the need for prior culturing. The present invention is convenient, rapid, cost-effective, does not need prior expertise to handle, has excellent selectivity and sensitivity. The present invention has the potential to improve patient outcomes and help reduce further evolution of antimicrobial resistant microorganisms.

28 Claims, 9 Drawing Sheets

METHOD FOR TESTING OF ANTIBIOTIC SUSCEPTIBILITY IN MICROORGANISMS

FIELD OF THE INVENTION

The present invention relates to a diagnostic method for determining antibiotic susceptibility in microorganisms and diagnostic tools thereof. Specifically, the present invention relates to a rapid, diagnostic method for testing antibiotic susceptibility in microorganisms based on phenotypic screening of growth of microorganisms in the presence of antibiotics performed directly on clinical samples with excellent selectivity and sensitivity.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Antibiotic sensitivity or antibiotic susceptibility is the susceptibility of microorganisms, often bacteria, to antibiotics. As susceptibility can vary even within a species, with some strains being more resistant than others, Antimicrobial Susceptibility Testing (AST) is usually carried out to determine which antibiotic will be most successful in treating an infection in vivo. In the absence of correctly predicting the antibiotic susceptibility profile of the microorganism, incorrect use or over prescription of antibiotics leads to the development of resistance in microorganisms. Antibiotic resistance of a microorganism refers to the organism's ability to resist the effect of antimicrobial drugs that were developed to treat infections caused by microorganisms. The development of antibiotic resistance in microorganisms is an inevitable biological process (Zaman S. et al., 2017) which occurs by various genetic and molecular mechanisms. Antibiotic resistance has thus become a global challenge and health concern.

While there are several scenarios where antibiotics are misused, the one that stands out are in the treatment of Urinary Tract Infections (UTI). UTI is the second highest infection in the human body affecting 150 million people globally and there has been a rise in antibiotic resistance in UTI-associated bacteria. Of late, fluoroquinolone resistant *E. coli* and carbapenem resistant *Klebsiella* have become a cause of concern for the successful treatment of UTI. India, with a population of 1.3 billion and only 75,000 hospitals, the healthcare setup is severely marred. Poor healthcare and diagnostic facilities further ramify its severity. Routine empirical treatment without identifying the bacteria and associated antibiotic susceptibility pattern of the uropathogen is a common practice, attributed mainly to the lack of urine culture facility in low resource settings. The grave diagnostic scenario resonates with many low and middle income countries (LMIC) and renders India as the largest contributor to antimicrobial resistance (AMR) in the world. The rampant rise of AMR is also attributed to gaps in the existing methods of antibiotic susceptibility testing. Propelled by misuse or rather, ignorant use of antibiotics, this problem warrants diagnostics that can quickly elucidate vital information about the infectious pathogen and the associated antibiotic susceptibility to aid clinicians take more informed and targeted treatment decisions. With 70% of population living in rural India, to be of real impact the diagnostic system must detect antibiotic susceptibility near point of care, without extensive training and sophisticated instrumentation, unlike urban settings or developed countries.

The AST market has several products based on the method they employ for testing that include automated systems, discs, MIC strips and media. Most extensively used method to determine antibiotic susceptibility involve culture tests based on the phenotypic growth of the bacteria, which require three days to arrive at the conclusion (Puttaswamy S. et al., 2018). Although culture-based growth methods are the most widely used systems for AST, a few sophisticated high-end labs and hospitals employ automated test machines such as Vitek 2.0 from Biomeriux Technologies, Phoenix from BD etc. These instruments work on the measurement of light attenuation by optical scanner for growth/no growth of bacteria in micro-wells with different antibiotics. The current methods despite being effective suffer from numerous shortcomings such as long waiting period for results, high infrastructure and capital cost, and intensive training, thus limiting their usage and therefore defeating the purpose of AST, and hence AMR.

Molecular methods which perform similar tasks within 4 hours are based on identification of genetic and molecular markers (James H. et al., 2009). These methods are based on various principles like identification of genetic markers/ DNA/RNA sequences by polymerase chain reaction, identification of certain metabolites by biochemical tests, and the like. However, these tests require sophisticated instruments and need prior expertise to handle (Karan Syal et al., 2017). Additionally, as bacterial genomes and molecular machineries are constantly evolving, routine molecular diagnostics methods might provide false information further contributing to AMR. Thus, detection methods based on the phenotypic growth of the bacteria which are independent of the genetic or molecular markers are always a step ahead. Therefore, currently available AST techniques fail to provide a robust diagnostic tool and method for rapid diagnosis while helping keep AMR in check. There is a need in the art to develop a method for determining antibiotic susceptibility in pathogens, which can overcome the deficiencies associated with the known arts.

Thus, there is an urgent need in the art for a rapid AST diagnostic tool and method having excellent selectivity and sensitivity that can rapidly predict the antibiotic susceptibility profile of a microorganism for rendering an effective control of antimicrobial resistance. Preferably, such tools and methods should be affordable, should not require tedious culturing procedures, lengthy waiting periods for results, or any use of sophisticated, expensive equipments or extensive training for medical personals. The tools and methods should preferably be easy to use by a minimally trained healthcare worker and should be able to deliver results in a rapid and reliable manner.

OBJECTS OF THE INVENTION

An object of the present invention is to provide reliable, affordable, accessible, point-of-care diagnostic tools and a diagnostic method for determining antibiotic susceptibility in microorganisms which can overcome the deficiencies associated with the present art.

Another object of the present invention is to provide diagnostic tools and a diagnostic method that is superior to the routine genotypic and molecular approaches currently existent in the art and will allow clinicians to initiate targeted antibiotic therapy, improve patient outcomes, lower hospital costs, and help reduce further evolution of antimicrobial resistance occurring due to over-prescription and misuse of antibiotics.

An object of the present invention is to provide novel diagnostic tools and method for determining antibiotic susceptibility in microorganisms based on a phenotypic screening of the growth of microorganism in the presence of one or more antibiotics.

Another object of the present invention is to provide a reliable method for determining susceptibility of microorganisms to antibiotics directly on clinical samples which is rapid, has excellent selectivity and sensitivity, is cost-effective, does not need prior expertise to handle, is convenient to use, improves patient outcomes, and helps reduce further evolution of antimicrobial resistance microorganisms.

Another object of the present invention is to provide a diagnostic system for determining antibiotic susceptibility of microorganisms in a clinical sample which is easy and convenient to use, is reliable, rapid and has excellent selectivity and sensitivity.

Still another object of the present invention is to provide diagnostic kits for determining antibiotic susceptibility of microorganisms in a clinical sample which is easy and convenient to use, is reliable, and has excellent selectivity and sensitivity.

Yet another object of the present invention is to provide a diagnostic tool that is superior to the tools and techniques currently existing in the art for providing a reliable and accurate measure of minimal inhibitory concentration (MIC) values in about 2 hours leading to rapid initiation of appropriate care by medical personnel.

SUMMARY OF THE INVENTION

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

One aspect the present disclosure relates to a diagnostic method for determining antibiotic susceptibility in microorganisms in a rapid and reliable manner, based on a phenotypic screening of the growth of microorganism in the presence of an antibiotic and works directly on clinical samples obliterating the need for any prior culturing of samples.

Another aspect of the present disclosure provides nanoprobes made up of gold nanoparticles having size in the range of 15 nm to 50 nm conjugated to antibodies and glucose oxidase for determining antibiotic susceptibility in microorganisms in a rapid and reliable manner. The antibodies are directionally bound to the gold nanoparticles through Fc region thereby maintaining the binding sites intact.

Another aspect of the present disclosure provides a method for determining antibiotic susceptibility of a microorganism comprising the steps of: a) adding a sample to nanoprobes in the presence of an antibiotic for 30 min to 90 min at a temperature in the range of 35° C. to 37° C. along with one control set incubated under similar conditions in the absence of an antibiotic; b) separating the nanoprobes bound to the microorganism in the sample from the unbound nanoprobes by filtration or washing; c) recovering the nanoprobe-microorganism complex of step (b) using sodium acetate buffer 10 mM having pH in the range of 4.5 to 5.5; d) incubating the recovered nanoprobe-microorganism complex with glucose solution of 50 to 150 mM concentration at a temperature of 37° C. for 5 min to 15 min; e) adding a seed solution to the solution of step (d) and allowing the solution to incubate for a period of 15 min to 25 min; and f) detecting the colour change and colour intensity of the solution of step (e) at UV-Visible spectrum and comparing it with the control for determining the antibiotic susceptibility of the microorganism; wherein the nanoprobes are gold nanoparticles conjugated to glucose oxidase and antibodies specific against the microorganism.

In another aspect of the present disclosure, the method of the present invention employs seed solution comprising gold nanoparticles in the range of 2 nm to 10 nm at a concentration in the range of 10-20 mM and $HAuCl_4$ solution at a concentration of 0.5 mM-2.5 mM.

In another aspect of the present disclosure, the method of the present invention requires glucose oxidase concentration in the range from 10 μU/ml to 10 U/ml for initiating growth of seed particles upon addition of seed solution to the nanoprobe-microorganism complex.

In another aspect of the present disclosure, the method of the present invention can be used for detecting the antibiotic susceptibility of the causal microorganisms of infections including but not limited to bacteria, fungi, and parasites.

In another aspect of the present disclosure, the method of the present invention can be used for determining antibiotic susceptibility of a causal microorganism selected from gram positive bacteria, gram negative bacteria and Myxobacteria.

In another aspect of the present disclosure, the method of the present invention determines susceptibility of a causal microorganism to an antibiotic selected from a group comprising Amikacin, Amoxicilin-Clavulanate, Ampicillin, Aztreonam, Benzylpenicillin, Cefazolin, Cefepime, Cefoxitin, Cefixime, Ceftazidime, Cefoperazone-Sulfobactam, Ceftriaxone, Cefotaxime, Cephalexin, Chloramphenicol, Ciprofloxacin, Cefuroxime, Colistin, Ertapenem, Erythromycin, Fosfomycin w/G6P, Gentamicin, Imipenem, Doxycycline, Daptomycin, Colistin, Levofloxacin, Linezolid, Nitrofurantoin, Norfloxacin, Oxacillin, Meropenem, Minocycline, Piperacillin-Tazobactam, Tigecycline, Tobramycin, Trimethoprim, Trimethoprim-Sulfomethoxazole, Teicoplanin, Tetracycline, Vancomycin.

In another aspect of the present disclosure, the method of the present invention determines susceptibility of a causal microorganism to an antibiotic directly in a sample selected from a group comprising blood, serum, urine, saliva, nasal discharge, sweat, plasma, semen, cerebrospinal fluid, tears, pus, amniotic fluid, lung aspirate, gastrointestinal contents, vaginal discharge, urethral discharge, chorionic villi specimens, epithelials, hair, and sputum.

In another aspect of the present disclosure, the method of the present invention determines susceptibility of a causal microorganism to an antibiotic by detecting the results at a single wavelength of 545 nm.

In another aspect of the present disclosure, the method of the present invention determines susceptibility of a causal microorganism to an antibiotic directly in a sample by detecting the change in colour of the sample solution from colourless to red upon incubation with the seed solution indicating the presence of seed particle growth and the increasing gradation of colour intensity is directly correlated to the increasing resistance of the microorganism to the antibiotic used in the method.

In another aspect of the present disclosure, the method of the present invention determines susceptibility of a causal microorganism to an antibiotic directly in a sample within 2 to 4 hours and most preferably within 2 hours.

Another aspect of the present disclosure provides a diagnostic system for determining antibiotic susceptibility in microorganisms comprising: (a) a cassette comprising at least one or more antibiotic well comprising an antibiotic and nanoprobes, and one control well devoid of any antibiotic; and (b) an analyzer for spectral determination and display of the results; wherein the nanoprobes are gold nanoparticles conjugated to glucose oxidase and antibodies specific against the microorganism.

In another aspect of the present disclosure, the system of the present invention comprises culture media for promoting growth of the microorganism in the wells of the cassette.

In another aspect of the present disclosure, the system of the present invention comprises antibiotic, nanoprobes and culture media present in lyophilized form in the wells of the cassette.

In another aspect of the present disclosure, the system of the present invention comprises more than one cassette for simultaneous run of more than one clinical sample.

In another aspect of the present disclosure, the system of the present invention comprises disposable cassettes that can be discarded after each run.

A further aspect of the present disclosure provides a kit for determining antibiotic susceptibility of a microorganism comprising: a) one or more nanoprobes; b) one or more antibiotics; c) buffer component having pH 4.5 to 5.5; d) seed solution; e) glucose solution of 50 mM to 150 mM; f) one or more capillary tubes for transfer of sample; g) one or more single use tubes or cassettes for carrying out the assay; h) one or more filtration devices; and i) reading material comprising directions for use and comprehending the results for determination of antibiotic susceptibility of the microorganism in the sample; wherein the nanoprobes are gold nanoparticles conjugated to glucose oxidase and antibodies against one or more microorganism; and wherein the antibodies are directionally bound to the gold nanoparticles through Fc region and maintain the binding sites intact.

Yet another aspect of the present disclosure provides a diagnostic tool that is superior to the tools and techniques currently existing in the art for providing a reliable and accurate measure of minimal inhibitory concentration (MIC) values in about 2 hours leading to rapid initiation of appropriate care by medical personnel.

Various objects, features, aspects and advantages of the inventive subject matter will become more apparent from the following detailed description of preferred embodiments, along with the accompanying drawing and figures in which numerals represent components.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION

Figure 1:
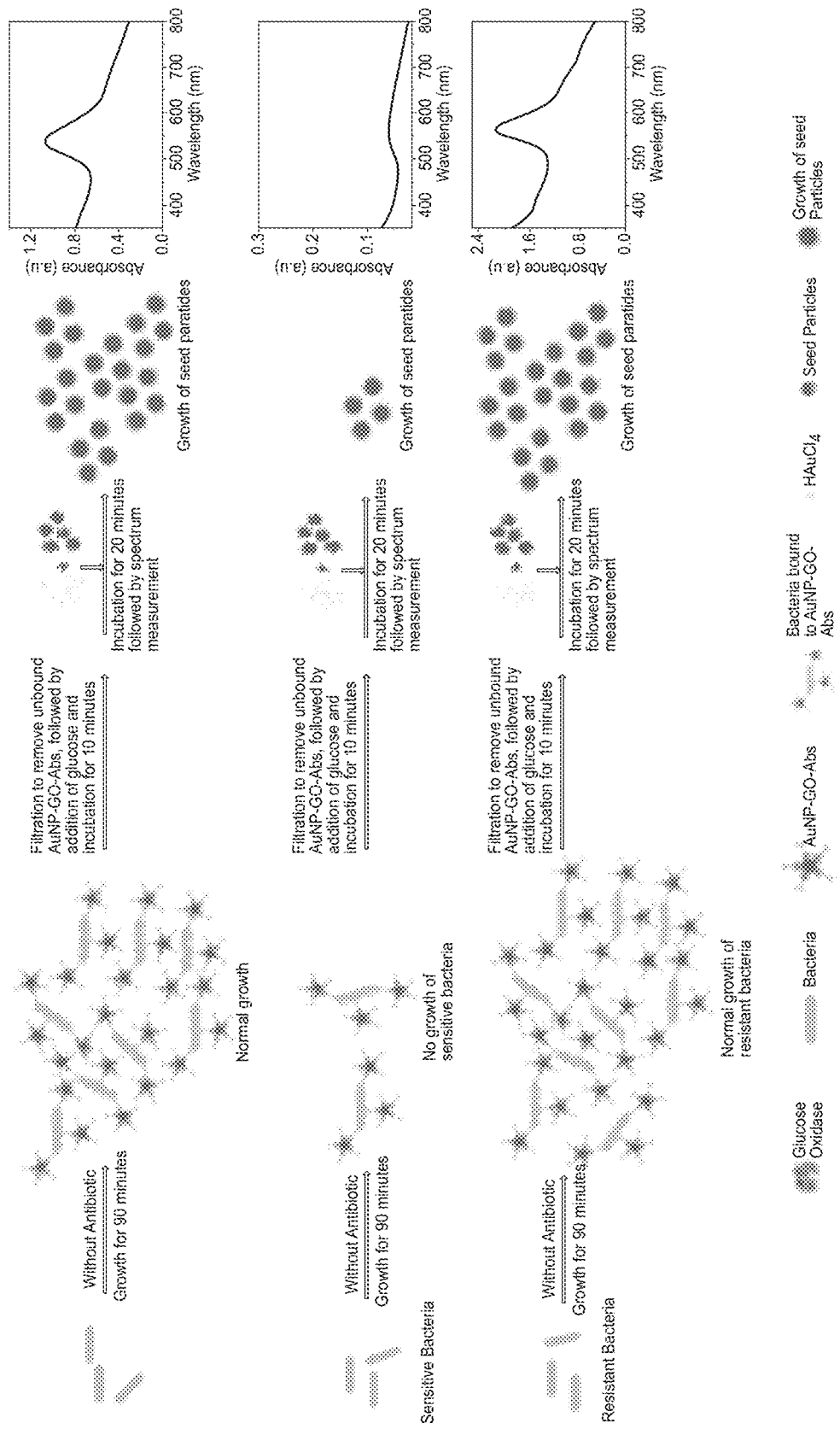
FIG. 1 is a schematic illustration of the principle of the diagnostic assay according to an embodiment of the present invention based on the mechanism of glucose oxidase-mediated growth of gold seed particles (2 nm-10 nm size) leading to colour formation. The figure provides schematics of growth of gold (Au) seed particle in the presence of hydrogen peroxide ($H_2O_2$) and the directly proportional relationship of colour intensity and bacterial growth.

The following is a detailed description of embodiments of the disclosure depicted in the accompanying drawings.

However, the amount of detail offered is not intended to limit the anticipated variations of embodiments; on the contrary, the intention is to cover all modifications, equivalents, and alternatives falling within the spirit and scope of the present disclosure as defined by the appended claims.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Various terms as used herein are shown below. To the extent a term used in a claim is not defined below, it should be given the broadest definition persons in the pertinent art have given that term as reflected in printed publications and issued patents at the time of filing. Where a definition or use of a term in an incorporated reference is inconsistent or contrary to the definition of that term provided herein, the definition of that term provided herein applies and the definition of that term in the reference does not apply.

It should also be appreciated that the present disclosure can be implemented in numerous ways, including as a system, a method or a device. In this specification, these implementations, or any other form that the invention may take, may be referred to as processes. In general, the order of the steps of the disclosed processes may be altered within the scope of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context requires otherwise, throughout the specification which follow, the word "comprise" and variations thereof, such as, "comprises" and "comprising" are to be construed in an open, inclusive sense that is as "including, but not limited to."

As used herein, the term 'about' used in the context of pH or other measurement or parameters described herein refers to the intrinsic variability due to reagents, apparatus, and human error in any measurement or apparatus or human interpretation of a parameter or result or those resulting from the standard deviation found in their respective testing measurements. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

As used herein, the term 'AuNP' refers to the gold nanoparticles, preferably having a size ranging from 2 nm to 40 nm.

As used herein, the term 'Ab' refers to an antibody or a fragment thereof against a microorganism.

As used herein, the term 'GOx' or 'Gox' refers to the enzyme glucose oxidase.

As used herein the term 'nanoprobe' or 'nanoprobes' is used interchangeably to refer to gold nanoparticles conjugated with glucose oxidase and antibodies against microorganisms, including bacteria. They are generally denoted by the notation 'AuNP-GOx-Ab' although not necessarily in the same order. At times it may be interchanged and denoted such as 'Ab-GOx-AuNP' or 'AuNP-Ab-GOx' or the like. All notations refer to the nanoprobes and their components and do not indicate any differences merely based on the order of referral.

As used herein the term 'diagnostic tool' is intended to include all inventions disclosed herein, such as a diagnostic system and its embodiments, diagnostic kit and its embodiments, and diagnostic method and its embodiments.

As used herein the term 'diagnostic devices' is intended to include all product inventions disclosed herein, such as a diagnostic system and its embodiments, and diagnostic kit and its embodiments.

As used herein the term 'diagnostic method' is used interchangeably with the terms 'assay method' or simply referred to as 'method' or the 'method of the present invention' or 'the method as disclosed herein' which all refer to the method invention disclosed in the present specification, unless explicitly stated otherwise.

As used herein, the term 'antibiotic susceptibility' refers to the susceptibility of microorganisms, often bacteria, to antibiotics. As the term 'antibiotic resistance' refers to a microorganism's ability to resist the effect of the antibiotic.

The present invention provides a diagnostic method, diagnostic system and a kit for determining antibiotic susceptibility in microorganisms. The present inventors have for the first time provided a rapid, sensitive, and reliable method for antibiotic susceptibility testing of causal microorganisms directly on the clinical samples without the need for any prior culturing, based on phenotypic screening of the bacteria in presence of major antibiotics being used currently.

The present invention relates to a method of determining antibiotic susceptibility of a microorganism based on a phenotypic approach thereby circumventing the pitfalls of genetic and molecular approaches. The present invention aims to detect glucose oxidase-mediated growth of gold nanoparticles (AuNP), also referred to as seed particles. Glucose oxidase (GOx) is an oxido-reductase enzyme which acts on β-d-glucose in the presence of oxygen to form glucono-δ-lactone, which is converted to gluconic acid and hydrogen peroxide ($H_2O_2$), as shown below in Schematic 1.

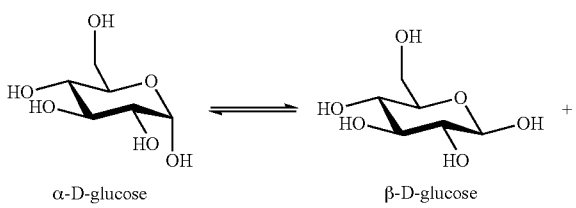

α-D-glucose        β-D-glucose

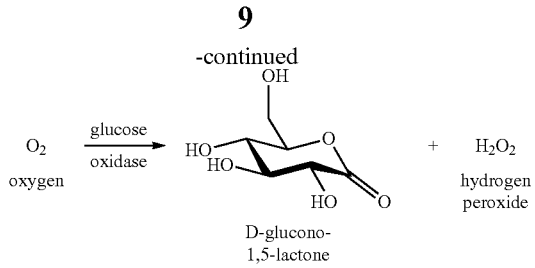

Schematic 1: Glucose Oxidase Catalyses Glucose to Produce Hydrogen Peroxide

The detailed reaction schematics with distinct process steps are also provided in FIG. 1. Hydrogen peroxide produced acts as a reductant of $HAuCl_4 \cdot 3H_2O$ for the formation of $Au^0$ on the Au seed particle surfaces.

$$HAuCl_4 + H_2O_2 \rightarrow Au^0 + O_2$$

In the present invention, the inventors have in an ingenious manner linked this phenomenon with the growth of a microorganism to provide a diagnostic tool for determining antibiotic susceptibility in causal microorganisms.

In an aspect of the present invention, nanoprobes of gold nanoparticles conjugated with polyclonal antibody and glucose oxidase, also referred to as AuNP-GOx-Ab, were specially designed and developed by the present inventors using EDC/NHS click chemistry and explained in detail in the Examples below. Further, another set of solution, referred to as the seed solution, was prepared for the invention wherein gold nanoparticles of about 2 to 10 nm size, and preferably of 3 nm to 8 nm size were employed as seed particles in a solution comprising $HAuCl_4$. The nanoprobes comprising glucose oxidase generated $H_2O_2$ in the presence of carbohydrate source and subsequently induced growth of the seed particles. The growth of the seed particles is tuned by glucose oxidase which generates hydrogen peroxide, which further reduces gold ions provided in the form of $HAuCl_4$ and deposits $Au^0$ on the seed particle surfaces, thereby increasing the size of the seed particles resulting in a change in the color of the solution from colorless to red in colour. The change of colour due to increase in size of nanoparticles from colourless to red which is visible to naked eye can also be quantified by monitoring the UV-Visible spectrum ranging from 400 nm to 900 nm wavelength or at a fixed wavelength of 545 nm. The objects of the present invention can be achieved by the assay method, diagnostic system and kits of the present invention that employ nanoprobes comprising gold nanoparticles coated with glucose oxidase and antibodies to the causal microorganism.

In an embodiment of the present invention, the gold nanoparticles for the seed solution range in size from 2 nm to 10 nm and most preferably in size from 3 nm to 8 nm.

Figure 2:
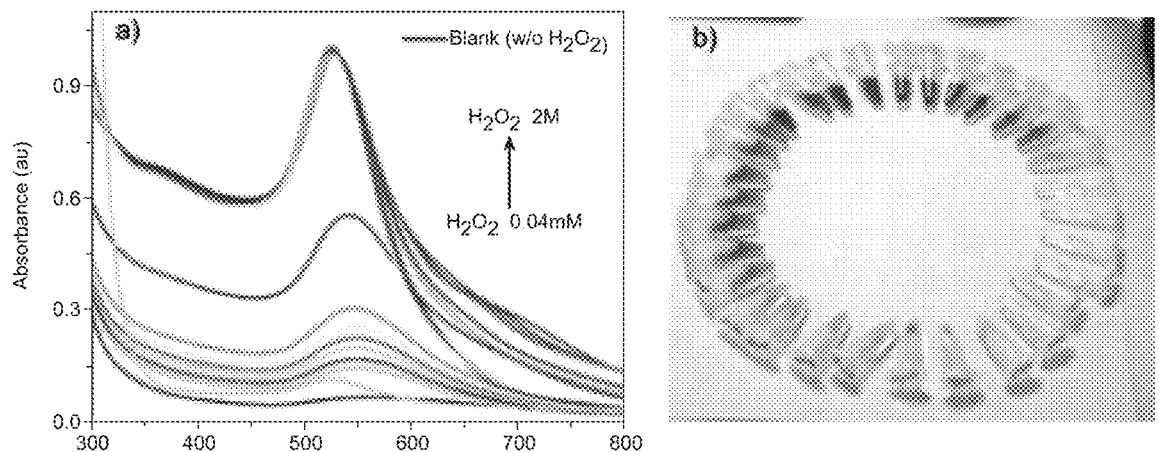
FIG. 2 is a graphic representation of a) an absorption spectrum for growth of seed particles at different concentrations of hydrogen peroxide, and b) photographic image showing colour change and colour intensity at different $H_2O_2$ concentrations, according to an embodiment of the present invention.

In a further aspect of the present invention, it is demonstrated that hydrogen peroxide initiates and controls the growth of gold seed particles. FIG. 2 provides a graphic representation of a) an absorption spectrum for growth of seed particles at different concentrations of hydrogen peroxide, and b) photographic image showing change in colour and colour intensity at different hydrogen peroxide concentrations, according to an embodiment of the present invention. $H_2O_2$ caused growth of seed particles by reducing $HAuCl_4$ and formation of $Au^0$ on the seed particles in a concentration dependent manner. FIG. 2 clearly demonstrates that the change in the colour of the solution is accompanied by increase in absorption at around 545 nm which reflects the intensity of the colour formed.

Figure 3:
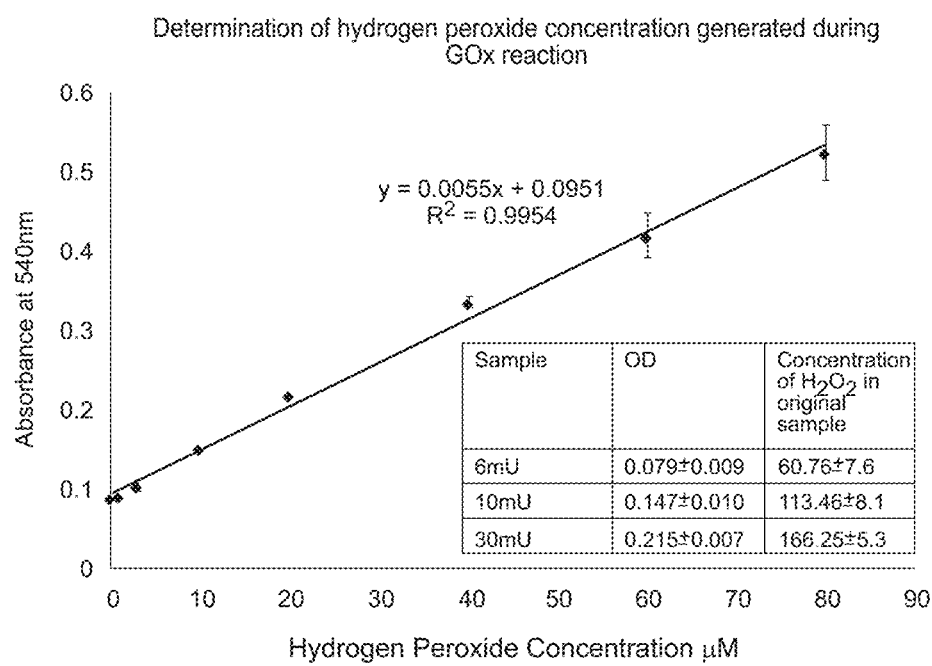
FIG. 3 is a graphic representation determining the amounts of $H_2O_2$ produced at varying concentrations (6 mU, 10 mU and 30 mU) of glucose oxidase (GOx) and fixed concentration of glucose (100 mM) within 10 minutes of incubation, according to an embodiment of the present invention.

In another aspect of the present invention, it is demonstrated that the amount of hydrogen peroxide produced is directly proportional to the amount of glucose oxidase present. FIG. 3 is a graphic representation determining the amounts of $H_2O_2$ produced at varying concentrations of glucose oxidase (6 mU, 10 mU and 30 mU) and fixed concentration of glucose (100 mM) within 10 minutes of incubation. Varying amounts of glucose oxidase incubated with a fixed amount of glucose resulted in generation of hydrogen peroxide to which the seed solution comprising seed particles and $HAuCl_4$ were introduced in the reaction mixture. After about twenty minutes of incubation, the absorption spectra of the solutions were monitored, as shown in FIG. 3.

Figure 4:
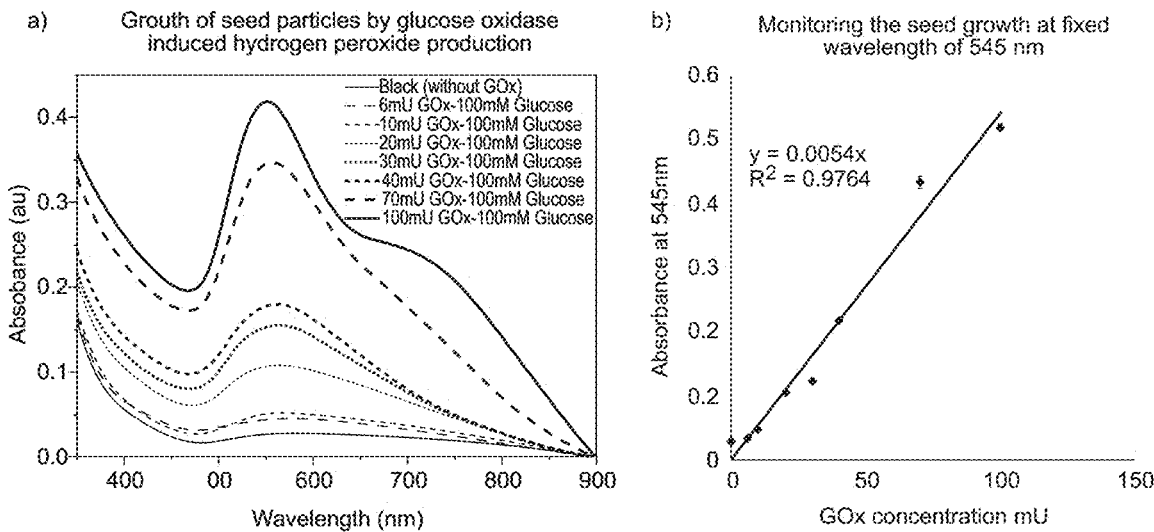
FIG. 4 is a graphic representation of a) UV-Visible spectra of seed particles growth by $H_2O_2$ generated with different concentrations of glucose oxidase, and b) absorbance values at 545 nm for determining seed particle growth by monitoring $H_2O_2$ generated at different GOx concentrations, according to an embodiment of the present invention.

In a further aspect of the present invention, the absorption spectra of the solutions with varying amounts of glucose oxidase incubated with a fixed amount of glucose resulted in generation of hydrogen peroxide which increased the size of the seed particles. FIG. 4 is a graphic representation of a) UV-Visible spectra of seed particles growth by $H_2O_2$ generated with different concentrations of glucose oxidase and b) absorbance values at 545 nm for determining seed particle growth by monitoring hydrogen peroxide generated at different GOx concentrations. Blank reaction lacking glucose oxidase did not show the growth of seed particles thereby confirming that glucose oxidase is the only source for production of hydrogen peroxide and eventual growth of the seed particles. The growth of seed particles is directly proportional to the glucose oxidase concentration evident by the increase in the absorption peak intensity at around 545 nm in FIG. 4 (a) and the slope in FIG. 4 (b).

Figure 5:
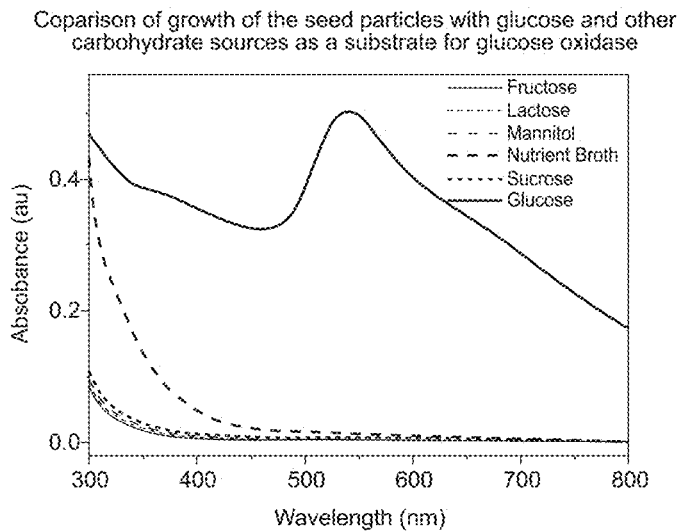
FIG. 5 is a graphic representation of differences in growth of gold seed particles and specificity of GOx towards glucose and other carbohydrate sources as a substrate for $H_2O_2$ production, according to an embodiment of the present invention.

In an aspect of the present invention, glucose as a carbohydrate source is specific for the glucose oxidase of the nanoprobes. FIG. 5 is a graphic representation of differences in growth of seed particles and specificity of glucose oxidase towards glucose and other carbohydrate sources as a substrate for hydrogen peroxide production. As seen in FIG. 5, the carbohydrate sources like sucrose, fructose, lactose, mannitol and nutrient broth at concentrations similar to that of glucose did not show growth of the seed particles.

In an embodiment of the present invention, nanoprobes were developed by conjugating glucose oxidase and the antibodies against microorganism, preferably bacteria, on the surface of gold nanoparticles having a size in the range of 15-40 nm. Preferably, the size of the nanoparticles is about 20 nm.

Figure 6:
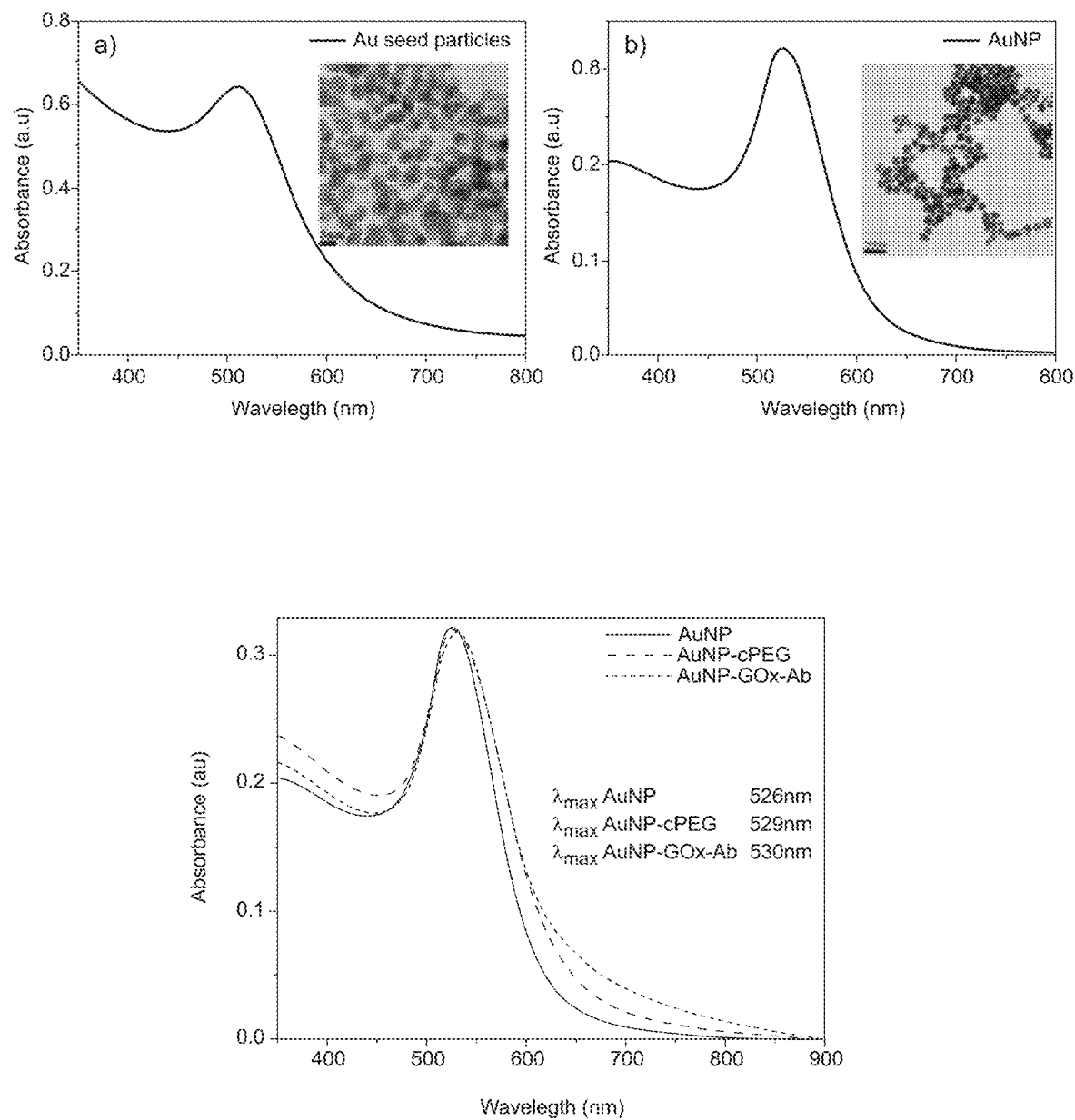
FIG. 6 is a graphic representation of a) UV-Visible spectrum and TEM image of 5 nm-sized gold seed particles, b) UV-Visible spectrum and TEM image of 24 nm-sized gold nanoparticles used for synthesis of the nanoprobes (AuNP-GOx-Ab), c) UV-Visible spectra of bare gold nanoparticles (AuNP), carboxyl gold nanoparticles (AuNP-cPEG), and carboxyl gold particles loaded with glucose oxidase and polyclonal antibodies against a group of bacteria (*E. coli, K. pneumoniae, P. aeruginosa, E. faecalis*) (AuNP-GOx-Ab), according to an embodiment of the present invention.

In an embodiment of the present invention, glucose oxidase and antibodies were loaded on the carboxyl gold nanoparticles using the high efficiency and stability protein cross linking with (1-Ethyl-3-[3-dimethylaminopropyl]carbodiimide hydrochloride) (EDC) involving N-hydroxysuccinimide (NHS). Successful loading of the glucose oxidase and the antibodies on the nanoparticles surface is evident from the shift in the peak of absorbance of the nanoparticles colloidal solution (FIG. 6). FIG. 6 provides a graphic representation of a) UV spectrum and TEM image of 5 nm gold seed particles, b) UV spectrum and TEM image of 24 nm gold nanoparticles used for synthesis of AuNP-GOx-Ab, c) UV spectra of bare gold nanoparticles (AuNP), carboxyl gold nanoparticles (AuNP-cPEG), and carboxyl gold particles loaded with glucose oxidase and polyclonal antibodies against a group of bacteria (E. coli, K. pneumoniae, P. aeruginosa, E. faecalis) (AuNP-Gox-Ab) prepared according to an embodiment of the present invention.

In an embodiment of the present invention, the nanoprobe is of carboxyl type or amine type. Preferably, the nanoprobe is a carboxyl gold nanoparticle loaded with glucose oxidase and a polyclonal antibody against a range of bacteria comprising *E. coli, K. pneumoniae, P. aeruginosa* and *E. faecalis*.

Yet another aspect of the present disclosure provides nanoprobes made up of gold nanoparticles conjugated to antibodies such that the antibodies are directionally bound to the gold nanoparticles through Fc region thereby maintaining the binding sites intact. Therefore much less antibodies are needed for efficient binding compared with other techniques like covalent binding and physical adsorption.

In another embodiment of the present invention, the nanoprobes comprise antibodies against a microorganism of polyclonal, monoclonal or recombinant types. Preferably, the antibodies against a microorganism of interest may be formed by various methods known in the art. Preferably, polyclonal antibodies are a heterogeneous mix of antibodies, derived from the immune response of multiple B-cells, and each one recognizes a different epitope on the same antigen. Monoclonal antibodies come from a single B-cell parent clone and therefore only recognize a single epitope per antigen. Recombinant antibodies are developed in vitro using synthetic genes which allow for optimized binding.

Figure 7:
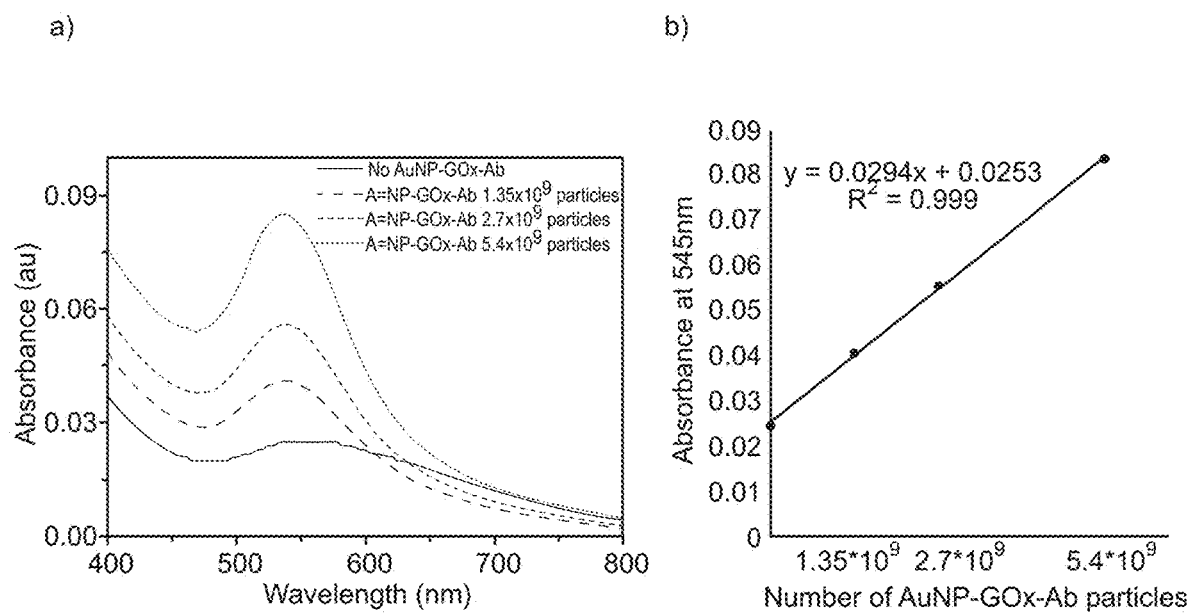
FIG. 7 is a graphic representation of a) UV-Visible spectra of growth of gold seed in the presence of $H_2O_2$ generated with varying concentrations of the nanoprobe comprising polyclonal antibody against a group of bacteria (*E. coli, K. pneumoniae, P. aeruginosa, E. faecalis*) and b) growth of gold seed particle in the presence of varying concentrations of nanoprobe at a wavelength of 545 nm, according to an embodiment of the present invention.

In an embodiment of the present invention, the functionalized nanoprobes were checked for glucose oxidase activity and the effect of varying concentrations of the nanoprobes on growth of the seed particles. The intensity of the colour formed was found to strictly correlate to the concentrations of the nanoprobes as confirmed by recording absorption spectra of the solutions which showed increase in the peak at around 545 nm. FIG. 7 is a graphic representation of a) UV-Visible spectra of growth of seed particle in the presence of $H_2O_2$ generated with varying concentrations of the nanoprobes, and b) growth of seed particle in varying concentrations of the nanoprobes prepared according to an embodiment of the present invention.

The present invention provides a method to determine antibiotic susceptibility of microorganism directly from a clinical sample without the need for any culturing of the clinical sample. In one aspect of the present invention, the nanoprobes were incubated with a clinical sample in presence of an antibiotic so as to allow binding of the nanoprobe with the microorganism. Simultaneously, a control was also set up wherein the nanoprobes were allowed to bind to the microorganism in the sample in the absence of an antibiotic. During incubation the nanoprobes bind to the microorganisms in a proportional manner. If the microorganisms are sensitive to the antibiotic, fewer nanoprobes are bound as the number of microorganisms is less. In case of resistant microorganisms, high amount of nanoprobes are bound, as the microorganisms are unaffected by the antibiotic. The microorganisms bound nanoprobes are separated from the unbound nanoprobes by filtration using filters of 0.45 to 0.22 μm pore size. This step removes the unbound nanoprobes as they are much smaller in diameter than the filter pores and could pass easily through the membrane. The nanoprobes bound to microorganism cells form too large complexes to penetrate through the pores and remain on the membrane filter. The nanoprobe-microorganism complexes captured on the membrane surface were then recovered by injecting buffer from the opposite direction. The recovered complexes were then incubated with glucose solution in sodium acetate buffer and incubated at 37° C. for ten minutes to allow generation of hydrogen peroxide.

Subsequently, a seed solution comprising gold nanoparticles was added to induce growth of the seed particles. The solution was left undisturbed for about 20 minutes. The glucose oxidase concentration is proportional to the number of bacteria and produces equivalent amount of hydrogen peroxide. The amount of hydrogen peroxide produced determines the colour formed due to the growth of seed nanoparticles. Glucose oxidase thus controls the colour intensity, which in turn, is dependent on the growth of bacteria.

Figure 9:
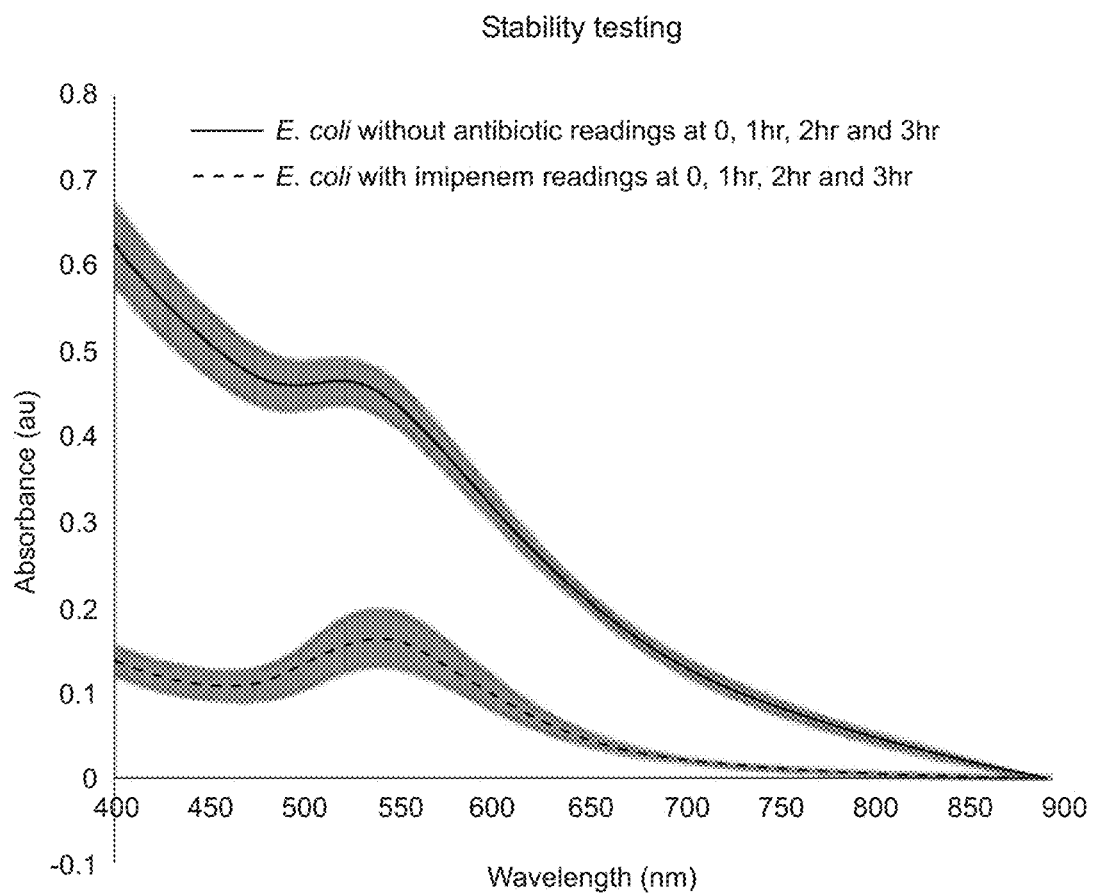
FIG. 9 is a graphic representation of UV-Visible spectra for the stability test of the diagnostic method for determination of antibiotic sensitivity for *E. coli* in the absence and presence of an antibiotic (imipenem) at 0 min, 1 h, 2 h and 3 h time intervals, according to an embodiment of the present invention.

The growth of the seed particles is tuned by glucose oxidase which generates hydrogen peroxide, which further reduces gold ions provided in the form of HAuCl4 around the seed nanoparticles thereby increasing their size and changing color of the solution. The growth of seed nanoparticles and the intensity of colour formed were determined by recording an absorption spectrum for each sample. Control for the assay method comprises solutions in the absence of any antibiotic and thus, show the highest colour development. FIG. 9 is a graphic representation of UV-Visible spectra for antibiotic sensitivity test of *E. coli* without antibiotics and with the antibiotic, imipenem, according to an embodiment of the present invention. FIG. 9 clearly shows that the bacteria grown without the antibiotic show significant growth of the seed nanoparticles as evidenced by the intensity of the peak in an absorption spectrum. However, when antibiotic is present, the growth of the seed nanoparticles is much less as bacteria do not grow. In this case, the intensity of the peak in the absorption spectrum is significantly lower compared to the panel with bacteria grown in absence of the antibiotic.

In an embodiment of the present invention, the method for determining antibiotic susceptibility of a microorganism directly in a sample comprises the steps of:
  a) adding a sample to nanoprobes in the presence of an antibiotic for 30 minutes to 90 minutes at a temperature in the range of 35° C. to 37° C. along with one control set incubated under similar conditions in the absence of an antibiotic;
  b) separating the nanoprobes bound to the microorganism in the sample from the unbound nanoprobes by filtration or washing;
  c) recovering the nanoprobe-microorganism complex of step (b) using sodium acetate buffer of 10 mM having pH in the range of 4.5 to 5.5;
  d) incubating the recovered nanoprobe-microorganism complex with glucose solution of 50 to 150 mM concentration at a temperature of 37° C. for 5 minutes to 15 minutes;
  e) adding a seed solution to the solution of step (d) and allowing the solution to incubate for a period of 15 to 25 minutes; and
  f) detecting the colour change and colour intensity of the solution of step (e) at UV-Visible spectrum and comparing it with the control for determining the antibiotic susceptibility of the microorganism;
  wherein the nanoprobes are gold nanoparticles conjugated to glucose oxidase and antibodies specific against the microorganism.

In an embodiment of the present invention, the seed solution comprises gold nanoparticles and $HAuCl_4$. The gold nanoparticles are preferably in a size range from 2 nm to 10 nm, more preferably in the size range of 3 nm to 8 nm and most preferably at about 5 nm. In another embodiment of the invention, the concentration of gold nanoparticles in the seed solution is in a range from 10 nM to 20 nM and $HAuCl_4$ solution is in a concentration range from 0.5 mM to 2.5 mM.

In another embodiment of the present invention, the size of the gold nanoparticles used for making nanoprobes is in the range of 15 nm to 50 nm. Preferably, the size of the gold nanoparticles in about 20 nm.

In another embodiment of the present invention, the concentration of glucose oxidase required for initiating growth of seed particles is in the range from 10 µU/ml to 10 U/ml. The glucose oxidase is present on the surface of the gold nanoparticles as shown in FIG. 1.

In another embodiment of the present invention, the nanoprobes comprise antibodies against a microorganism of polyclonal, monoclonal or recombinant types. Preferably, the antibodies against a microorganism of interest may be formed by various methods known in the art. Preferably, polyclonal antibodies are a heterogeneous mix of antibodies, derived from the immune response of multiple B-cells, and each one recognizes a different epitope on the same antigen. Monoclonal antibodies come from a single B-cell parent clone and therefore only recognize a single epitope per antigen. Recombinant antibodies are developed in vitro using synthetic genes which allow for optimized binding.

In another embodiment of the present invention, the filtration of the nanoprobe bound microorganism and the unbound nanoprobes are separated by filtration carried out using a membrane having pore size of 200 nm to 450 nm diameter.

The present invention provides a method for detecting the antibiotic sensitivity profile of a microorganism directly in a sample. The term 'sample' as used herein refers to any sample that could contain an analyte for detection. Preferably the sample is in liquid form or can be changed into a liquid form. The sample is selected from a group including but not limited to blood, serum, urine, saliva, nasal discharge, sweat, plasma, semen, cerebrospinal fluid, tears, pus, amniotic fluid, lung aspirate, gastrointestinal contents, vaginal discharge, urethral discharge, chorionic villi specimens, epithelials, hair, and sputum. Preferably, the sample is urine. Samples may be buffered or may have their pH altered prior to being subjected to the methods of the invention. Preferably, the urine sample may be mixed with a culture growth media such as Mueller-Hinton broth and the resulting pH is in a range of 7 to 7.4.

In an embodiment of the present invention, the sample volumes can range from between about 200 µL to about 300 µL and preferably about 250 µL.

Figure 8:
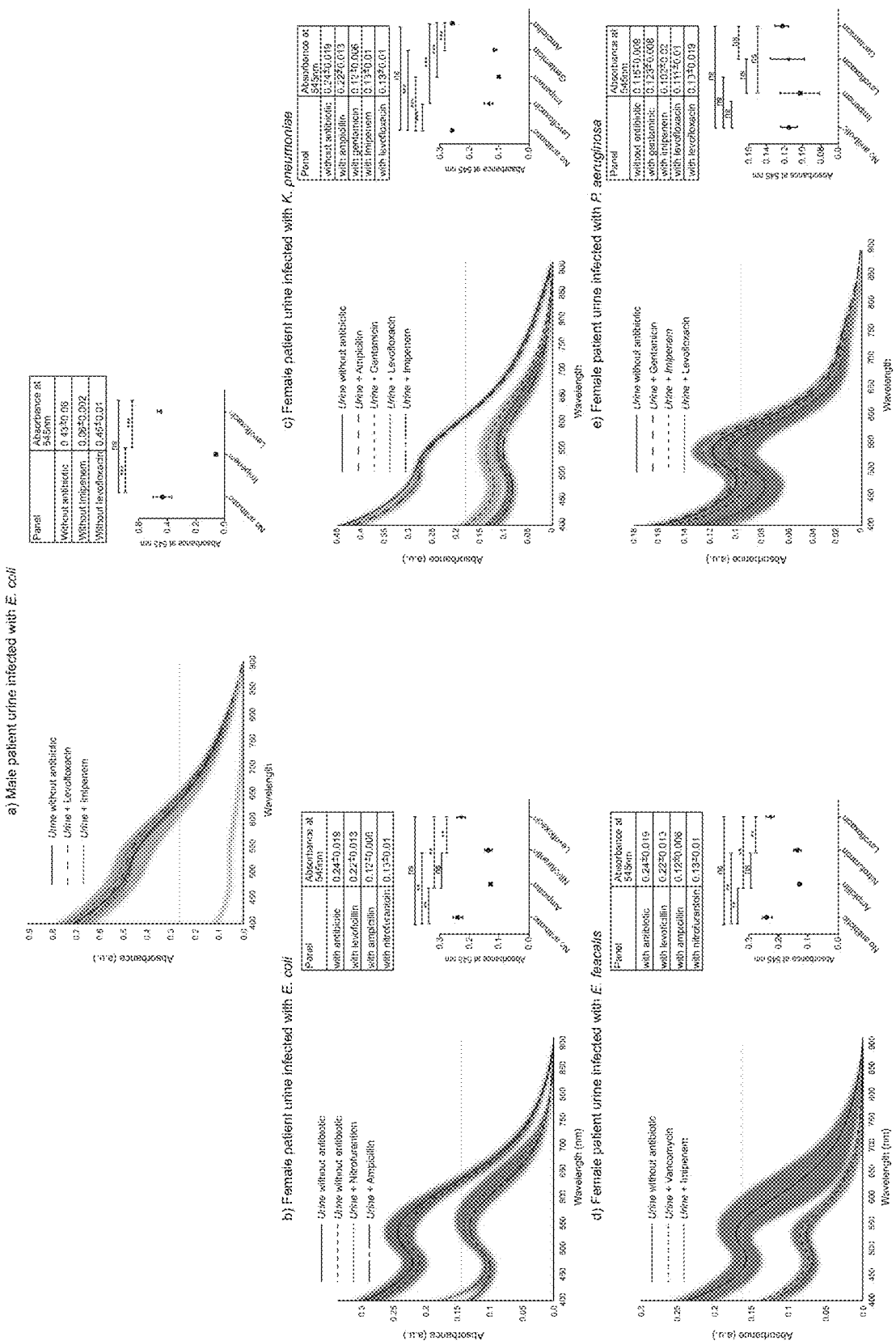
FIG. 8 is a graphic representation of UV-Visible spectra for determining antibiotic sensitivity of microorganism ((*E. coli, K. pneumoniae, P. aeruginosa, E. faecalis*) in a patient urine samples to different antibiotics, according to an embodiment of the present invention. The graph shows the dot plots and reading from the same assays monitored at a fixed wavelength of 545 nm with ,* p<0.05, and ns—not significant.

In an embodiment of the present invention, the susceptibility of the causal microorganism to any antibiotic can be determined. The choice of antibiotic resides on the prevalent antibiotic resistance of the microorganism known in the art or to determine for any other purpose as deemed necessary by the clinician (FIG. 8). Preferably, the antibiotic is selected from a group comprising Amikacin, Amoxicilin-Clavulanate, Ampicillin, Aztreonam, Benzylpenicillin, Cefazolin, Cefepime, Cefoxitin, Cefixime, Ceftazidime, Cefoperazone-Sulfobactam, Ceftriaxone, Cefotaxime, Cephalexin, Chloramphenicol, Ciprofloxacin, Cefuroxime, Colistin, Ertapenem, Erythromycin, Fosfomycin w/G6P, Gentamicin, Imipenem, Doxycycline, Daptomycin, Colistin, Levofloxacin, Linezolid, Nitrofurantoin, Norfloxacin, Oxacillin, Meropenem, Minocycline, Piperacillin-Tazobactam, Tigecycline, Tobramycin, Trimethoprim, Trimethoprim-Sulfomethoxazole, Teicoplanin, Tetracycline, Vancomycin In an embodiment of the present invention, the determination of antibiotic susceptibility of a microorganism is for an organism selected from a group of bacteria, fungi, and parasites. Preferably, the microorganism is gram positive bacteria, gram negative bacteria, or Myxobacteria. Preferably, the method targets critical microorganisms including but not limited to *E. coli* resistant to carbapenem, *Klebsiella* spp resistant to carbapenem, *Pseudomonas* spp resistant to carbapenem, and vancomycin-resistant *Enterococcus*.

In an embodiment of the present invention, the microorganism is gram positive bacteria selected from *Staphylococcus, Streptococcus, Entreococcus, Corynebacterium, Listeria, Bacillus, Nocardia, Clostridium*, and *Actinomyces*. In another embodiment, the microorganism is gram negative bacteria selected from *E. coli, Klebsiella, Enterobacter, Salmonella, Shigella, Proteus, Citrobacter, Pseudomonas, Burkholderia, Stenotrophomonas, Acinetobacter, Vibrio, Yersinia, Legionella, Haemophilus, Bordetella, Brucella, Bartonella, Campylobacter, Bacteroides, Fusobacterium, Porphyromonas, Prevotella, Neisseria, Moraxella*, and *Veillonella*. In yet another embodiment, the microorganism is *Mycobacterium* having species *M. tuberculosis*, and *M. avium-intracellulare*.

In an embodiment of the present invention, the detection of the colour intensity of the solution in the final step of the method can be carried out at a single wavelength of 545 nm. This detection at a single fixed wavelength hastens the total time of the method and therefore provides a rapid readout of the results of the method.

In an embodiment of the present invention, the time taken for determination of antibiotic susceptibility in a microorganism directly in a sample is in the range of 2 hours to 4 hours and preferably within 2 hours. The conventional methods of culturing the sample and other methods currently existing in the art take around 48 to 72 hours.

The stability of the results of the method of the present invention are duly provided in FIG. 9, which shows spectrums obtained at the end of an assay (0 min), 1 hour, 2 hour and 3 hours. It was observed that the spectrums for without antibiotics panel and imipenem panel maintain different patterns even after 3 hours duly demonstrating the stability of the results obtained by the method of the present invention for at least 3 hours and beyond, after completion of the assay.

In an embodiment of the present invention, the antibiotic susceptibility of a microorganism is qualitatively detected by the change in colour of the solution in the final step upon incubation from colourless to red colour which indicates the growth of the seed particle and the antibiotic susceptibility of a microorganism is quantified by monitoring the increasing gradation of colour intensity which is directly correlated to the increasing resistance of the microorganism to the antibiotic used in the method compared with control (no antibiotic). Preferably the colour change and colour intensity is monitored in the absorption spectra (UV-Visible spectra). Preferably, a single wavelength absorbance at 545 nm can also be used for reducing the time taken for result readouts. The crude results can be viewed by unaided eye by the appearance and colour of the solutions. For quantitative interpretation, the intensities of the solution are determined at 545 nm and co-related to the antibiotic susceptibility of the bacteria in the sample against a control (nanoprobe-bacteria complex formed in the absence of any antibiotic). The control (bacteria grown without the antibiotic) shows significant growth of the seed nanoparticles with high intensity of the peak in an absorption spectrum. In case of sensitive bacteria, when antibiotic is present, the growth of seed nanoparticles is comparatively lower than control as bacteria do not grow. In this case, the intensity of the peak in the absorption spectrum is significantly lower compared to the control panel. In case of antibiotic resistant bacteria, growth is unaltered and the intensity of the peak in an absorption spectrum matches approximately with the peak of bacteria grown in the absence of antibiotic.

Figure 10:
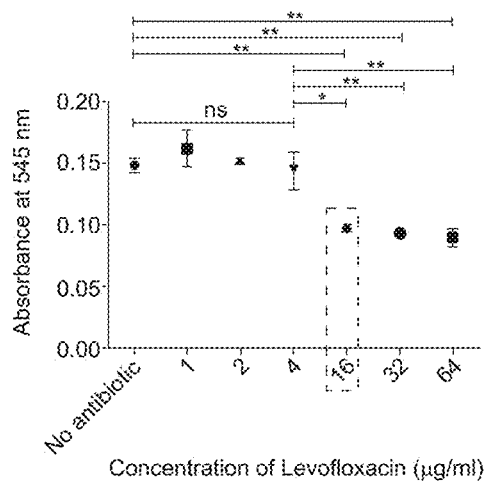
FIG. 10 is a graphic representation of the results of the diagnostic method according to an embodiment of the present invention, for determination of minimal inhibitory concentrations (MIC) of different combinations of antibiotic-clinical bacterial isolates.
Figure 10:
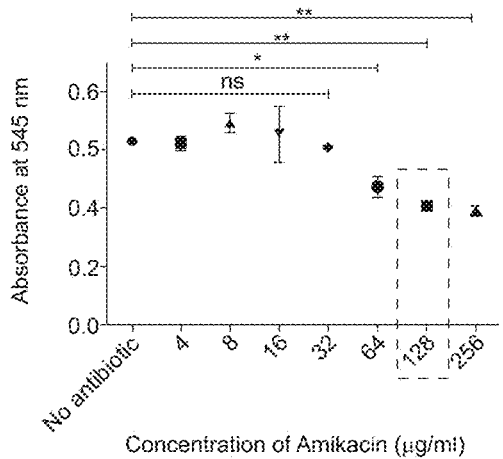
Figure 10:
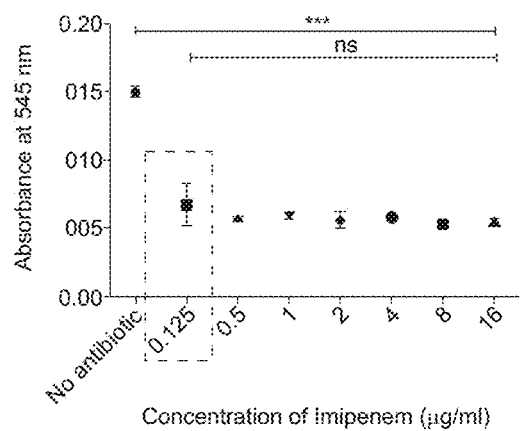

In clinical scenario, determination of minimal inhibitory concentration or MIC of particular antibiotic aids physicians in interpreting the antimicrobial susceptibility pattern quantitatively. For each antibiotic tested, the MIC obtained by the present method closely matches the MIC obtained with CLSI reference method of Microdilution. Different clinical isolates were tested against a range of antibiotics concentrations to determine MIC for each antibiotic. Table 2 in the Examples below provides details about the MIC determination rule for each combination used which in principle can be extended to all the other bacteria-antibiotic combinations. FIG. 10 is a graphic representation of the present method for MIC determination for different antibiotics-clinical bacterial isolates combination. The present diagnostic method accurately predicts MIC in up to 120 minutes for >16 antibiotics tested, making it way superior than the existing methods (Table 2 in the Examples).

Another aspect of the present invention provides a diagnostic system for rapid determination of antibiotic susceptibility in microorganisms comprising: (a) a cassette comprising at least one or more antibiotic well comprising an antibiotic and nanoprobes, and one control well devoid of any antibiotic; and (b) an analyzer for spectral determination and display of the results; wherein the nanoprobes are gold nanoparticles conjugated to glucose oxidase and antibodies specific against the microorganism (FIG. 11).

In an aspect, the diagnostic system is portable and relatively low dimension equipment, which can house one or more cassettes for testing samples. The diagnostic system is a multiplexed assay where one or more samples can be processed in a single run using one or more cassettes. Preferably, each cassette is used for running one sample. In a preferred embodiment, the system is an automated enzyme linked immunoassay method wherein results can be read on the display nit present on the system and requires very little human intervention. In a preferred embodiment, six samples can be run simultaneously in the diagnostic system. FIG. 11 provides a work flow inside a diagnostic system according to an embodiment of the present invention.

Figure 11:
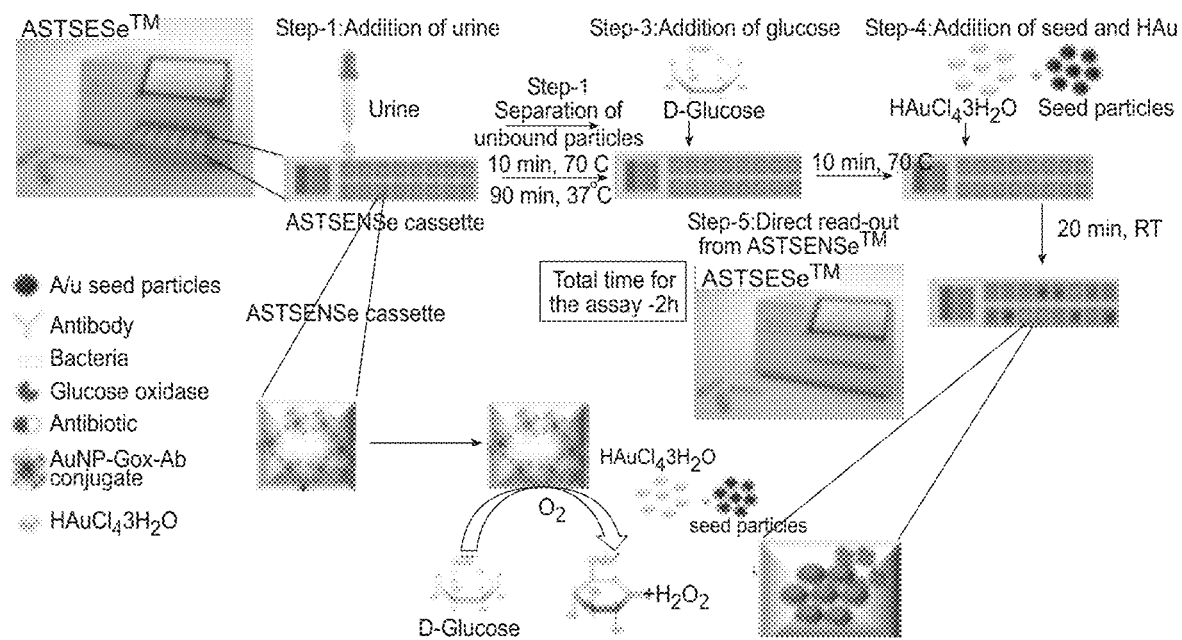
FIG. 11 is an illustration of the work flow of the diagnostic system according to an embodiment of the present invention.

A work flow inside the diagnostic system according to an embodiment of the present invention is also shown in FIG. 11. In a preferred embodiment, clinical sample is dispensed in the cassette by the automated system so that each well in the cassette receives identical volume. Each well of the cassette houses antibiotics and nanoprobes and bacterial growth medium in lyophilized form along with one well which lacks any of the antibiotic and serves as a control. The sample is allowed to incubate for about 60 minutes to 90 minutes in the well to allow bacterial growth and nanoprobe binding to the bacteria, which is directly proportional. Unbound nanoprobes are removed by an automated system via filtration or washing, followed by automated addition of fixed volume of glucose solution and allowed to incubate for 10 minutes. This is followed by addition of a fixed volume of seed solution and the solution undisturbed for 20 minutes to induce growth of the seed particles. Finally, the growth of seed nanoparticles and the intensity of colour formed are determined by the analyzer by monitoring the absorption spectrum or at a fixed wavelength of 545 nm for each well of the cassette, compared with control. Results of the assay run on a diagnostic system can be read on the display screen present on the system.

In an embodiment of the present invention, the size of the gold nanoparticles in the nanoprobes of the diagnostic system is in the range of 15 nm to 50 nm.

In an embodiment of the present invention, the nanoprobes have antibodies directionally bound to the gold nanoparticles through Fc region for maintaining the binding sites intact.

In an embodiment of the present invention, the wells of the cassette comprise culture media for promoting growth of the microorganism. Preferably the culture media is for promotion of growth of microorganism including bacteria, fungi and parasites.

In an embodiment of the present invention, the antibiotic, nanoprobes and culture media are present in lyophilized form in the wells of the cassette.

In an embodiment of the present invention, the system can house more than one cassette for simultaneous run of more than one clinical sample. Preferably, the system can house up to six cassettes and six samples can run simultaneously.

In an embodiment of the present invention, the cassettes are disposable and can be discarded after each run.

In an embodiment of the present invention, the analyzer in the system detects and analyses the results of the assay under UV-visible absorption spectrum or at a fixed wavelength of 545 nm or both. In an embodiment of the present invention, the results of the run can be printed or sent directly to the medical personnel and the patient.

In an embodiment of the present invention, the system is a completed automated system requiring minimal human intervention.

Another aspect of the present invention provides a kit for a reliable, rapid detection and differential identification of antibiotic susceptibility of the causal microorganism in a sample. The diagnostic method according to the present invention as disclosed herein can be provided as kits suitable for transport, point-of-care testing, and the like. Kits comprising diagnostic tools according to the invention may be packaged and sold together with instructions for use. The instructions may contain information on testing procedures, interpretation procedures, performance characteristics, information on the test device, storage and handling of the devices.

In an embodiment of the present invention, a kit for rapid determination of antibiotic susceptibility of a microorganism may include, for example: a) one or more nanoprobes; b) one or more antibiotics; c) buffer component having pH 4.5 to 5.5; d) seed solution; e) glucose solution of 50 mM to 150 mM; f) one or more capillary tubes for transfer of sample; g) one or more single use tubes or cassettes for carrying out the assay; h) one or more filtration devices; and i) reading material comprising directions for use and comprehending the results for determination of antibiotic susceptibility of the microorganism in the sample; wherein the nanoprobes are gold nanoparticles conjugated to glucose oxidase and antibodies against one or more microorganism; and wherein the antibodies are directionally bound to the gold nanoparticles through Fc region and maintain the binding sites intact.

In an embodiment of the present invention, the kit comprises nanoprobes comprising gold nanoparticles in the size ranging from 15 nm to 50 nm.

In an embodiment of the present invention, the kit comprises gold nanoparticles in the seed solution having a size in the range from 2 nm to 10 nm.

In an embodiment of the present invention, the kit comprises seed solution comprising gold nanoparticles at a concentration in the range from 10 nM to 20 nM and $HAuCl_4$ solution at a concentration in the range from 0.5 mM to 2.5 mM.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

EXAMPLES

The present invention is further explained in the form of following examples. However, it is to be understood that the following examples are merely illustrative and are not to be taken as limitations upon the scope of the invention.

Example 1

Growth of Gold Nanoparticles in the Presence of Hydrogen Peroxide ($H_2O_2$)

Gold nanoparticles of 5 nm diameter size were incubated in the presence of $HAuCl_4$ (1.25 mM) and varying concentrations of $H_2O_2$ for a time duration of 20 minutes. The color intensity of the solutions were then monitored using UV-Visible spectroscopy. As shown in FIG. 2(a), the absorbance maxima ($\lambda_{max}$) at around 545 nm intensified with increasing amounts of $H_2O_2$ confirming that the growth of gold nanoparticles is directly proportional to the concentration of $H_2O_2$. Further, the increasing concentration of $H_2O_2$ turns the solution red which is visible to the unaided eye, as shown in FIG. 2(b). The experiment confirmed that gold nanoparticles can be effectively used as seed particles.

Production of $H_2O_2$ Using Glucose Oxidase (GOx) and Glucose

Varying concentrations of GOx, namely, 6 mU, 10 mU and 30 mU and glucose (100 mM) were incubated at 37° C. for 10 minutes and the hydrogen peroxide produced was determined using a $H_2O_2$ assay kit (MAK165—SIGMA-ALDRICH). It was observed that 6 mU, 10 mU and 30 mUGOx generated 60.76±7.6, 113.46±48.1 and 166.25±5.3 µM $H_2O_2$, respectively, as shown in FIG. 3. The amount of $H_2O_2$ produced is directly proportional to the amount of GOx present in the system.

Sufficiency of $H_2O_2$ for Growth of Seed Particles 100 mM of glucose was incubated with varying concentrations of GOx for 10 minutes at 37° C. After 10 minutes, a final concentration of 4 nM seed particles (gold nanoparticles of size 5 nm) and 0.3 mM $HAuCl_4$ was introduced in the reaction mixture and incubated for 20 minutes at room temperature (37° C.). The absorption spectrum was taken for the solutions and provided in FIG. 4a. The growth of seed particles is evident from the increase in the absorption peak at around 545 nm in GOx concentration-dependent manner. Thus, it was confirmed that the concentration of $H_2O_2$ produced was directly proportional to the concentration of GOx.

FIG. 4b shows the absorbance values recorded at 545 nm for three independent experiments. It is clearly shown that the absorbance values at 545 nm increased with respect to the increasing concentrations of GOx. This shows that the growth of seed particles could be monitored at fixed wavelength too instead of taking the whole absorption spectra, reducing the down time in the method.

Specificity of Carbohydrate Source

Effect of carbohydrate sources including fructose, sucrose, lactose, mannitol, nutrient broth, and glucose at the concentration of 100 mM on the seed particles was evaluated. 100 mM of the carbohydrate source was incubated with 40 mU GOx for 10 minutes at 37° C. After 10 minutes, a final concentration of 4 nM seed particles (gold nanoparticles of size 5 nm) and 0.3 mM $HAuCl_4$ was introduced in the reaction mixture and incubated for 20 minutes at room temperature (37° C.). The absorption spectrum was taken for the solutions and provided in FIG. 5. The absorbance spectra clearly indicate an absence of growth of seed particles in any of the carbohydrate sources other than glucose. The specificity of the reaction towards glucose is confirmed.

Example 2

Preparation of Nanoprobes

Citrate stabilized 24 nm gold nanoparticles, confirmed with TEM, FIG. 6b, were modified with poly(ethylene glycol)2-mercapto ethyl ether acetic acid to form AuNP-cPEG also referred to as carboxylated gold nanoparticles. The AuNP-cPEG were then conjugated with GOx and polyclonal antibody (Ab) using EDC/NHS click chemistry (Jazayeri et al., 2016, Sensing and Bio-sensing research, 9 (17-22)). FIG. 6c shows that there is a 3 nm red shift in the surface plasmon resonance (SPR) peak from 526 nm to 529 nm after modification of AuNP with cPEG. This implies a successful surface modification of AuNP with cPEG. The conjugation of GOx and Ab on AuNP-cPEG nanoparticles was confirmed by the shift in the SPR absorbance peak as depicted in FIG. 6c. As shown in the FIG. 6c, the SPR absorption band for AuNP-cPEG was found to shift from 529 to 530 nm after the conjugation with GOx and antibody. These AuNP-GOx-Ab conjugate particles are referred to as nanoprobes.

Determination of GOx Activity of Nanoprobes

Nanoprobes prepared according to the Example above were taken in a concentration of $1.35 \times 10^9$, $2.7 \times 10^9$ and $5.4 \times 10^9$ were incubated with 100 mM glucose for 10 minutes at 37° C. to induce $H_2O_2$ production. Then, 4 nM gold seed particles (diameter 5 nm, confirmed by TEM, FIG. 6a) along with $HAuCl_4$ (0.3 mM) was added and incubated for 20 minutes to initiate growth of the seed particles in the presence of any $H_2O_2$ produced by the reaction in the solution. $H_2O_2$, as the GOx catalytic reaction product, stimulates the growth of 5 nm Au seeds through reducing $HAuCl_4$ and formation of $Au^0$ on the seed particle (AuNP) surface. The growth of the seed particles was determined and quantified using the results of the absorbance spectra as shown in FIG. 7(a). It is clear from the FIG. 7(a) & (b) that the intensity of the absorption spectrum at 545 nm increased with increase in the nanoprobes concentration. This confirms growth of seed particles as the concentration of nanoprobes increases due to increased concentration of $H_2O_2$.

Example 3

15 Antibiotic Susceptibility Testing of Clinical Samples

Urine samples of infected patients were obtained from Deenanath Mangeshkar Hospital and Research Center (DMHRC), Pune, India. The antibiotic susceptibility results obtained by the method of the present invention were simultaneously cross-checked with the gold standard microdilution method (CLSI. Performance Standards for Antimicrobial Susceptibility Testing. 26th ed. CLSI supplementM100S. Wayne, PA: Clinical and Laboratory Standards Institute; 2016). EUCAST break point rules (Version 9.0, valid from 01-01-2019) were strictly followed for the analysis and interpretation of the results (Table 1 indicates the break-point values provided by EUCAST). The concentration of the antibiotics used for the diagnostic method and the results obtained with different clinical samples are summarized in Table 1.

Assay of Clinical Samples of Male Patients Infected with E. coli

Urine sample of a male patient infected with E. coli ($10^4$ CFU/mL) was tested for antibiotic susceptibility/resistance to the antibiotics imipenem (carbapenem subgroup) and levofloxacin (fluoroquinolone class).

250 μL of urine sample was mixed with 250 μL of 2× Mueller-Hinton broth in autoclaved Eppendorf tubes. Respective concentrations of antibiotics as recited in Table 1 were added in each tubes along with one tube without antibiotic which served as a control for monitoring the growth of bacteria. 7-10 μL of the nanoprobes (AuNP-GOx-Ab) prepared in the Example 2 above was added to the mixture and allowed to incubate at 37° C. for 90 minutes to allow growth of bacteria. The solution was then passed through a membrane filter with a pore size of about 450 nm diameter to separate the bacteria bound to the nanoprobes from the unbound ones. The bacteria bound nanoprobes (nanoprobe-bacteria complex) captured on the membrane surface were then recovered by injecting 250 μL of sodium acetate buffer (10 mM, pH 5.1) from the opposite direction.

250 μL of the recovered bacteria-nanoprobe complexes were then incubated at 37° C. for 10 minutes with 50 μL glucose solution (final concentration 100 mM) for production of hydrogen peroxide. After 10 minutes, 150 μL of seed solution containing about 16 nM gold nanoparticles having about 5 nm size and 150 μL of 1.25 mM HAuCl$_4$ solution was added to induce growth of the seed particles and left for 20 minutes to allow growth of the seed particle. Finally, the growth of seed nanoparticles and the intensity of colour formed were determined by recording an absorption spectrum for each sample. FIG. 8(a) provides graphic representation of UV-Visible spectra for antibiotic sensitivity test of patient urine samples with different antibiotics, according to an embodiment of the present invention. The graph shows the dot plots and reading from the same assays monitored at a fixed wavelength of 545 nm with significance values ,* p<0.05, ns—not significant.

Clinical urine sample of a male patient containing E. coli grown in the presence of imipenem showed significantly lower intensity of the peak in the absorption spectrum compared to the levofloxacin panel and the control (antibiotic negative) panel. The growth of bacteria was inhibited in the presence of imipenem resulting in negligible binding of the nanoprobes to the bacteria resulting in significantly lower growth of the gold seed particles. This suggested that E. coli is sensitive to the concentrations of imipenem as used herein.

In contrast, the intensity of the peak in levofloxacin panel lie closer to the intensity of peak obtained in the cells grown without any antibiotic, which suggests that the bacteria is resistant to levofloxacin. Absorbance values provided in FIG. 8 (a) suggests that the assay could be monitored at a fixed wavelength as well. Absorbance at 545 nm for imipenem panel are significantly lower (p<0.05) than those obtained for levofloxacin and control (without antibiotics) panel.

Assay of Clinical Samples of Female Patients Infected with E. coli

Urine sample of a female patient infected with E. coli ($10^4$ CFU/mL) was tested for antibiotic susceptibility/resistance to the antibiotics ampicillin (penicillin class), levofloxacin (fluoroquinolone class) and nitrofurantoin. The assay method was similar to that done for the male clinical samples. FIG. 8 (b) provides the results obtained with the female patient urine samples.

Sample containing E. coli incubated in presence of either ampicillin or nitrofurantoin showed significantly lower intensity of the peak in the absorption spectrum compared to the levofloxacin panel and control (antibiotic negative) panel indicating that the bacteria was inhibited in the presence of ampicillin or nitrofurantoin. Negligible binding of the bacteria to the nanoprobes resulted in significantly lower growth of the seed particles suggesting that the causal E. coli in the sample is sensitive to the antibiotics ampicillin and nitrofurantoin at their respective concentrations (Table 1). In contrast, the intensity of the peak in levofloxacin panel lie closer to the intensity of peak obtained in the cells grown without any antibiotic, suggesting that the bacteria is resistant to levofloxacin. Absorbance values suggest that the assay could be monitored at a fixed wavelength at 545 nm where the ampicillin and nitrofurantoin panels exhibited a significantly lower intensity (p<0.05) than those obtained for levofloxacin and without antibiotics panel.

Assay of Clinical Samples of Female Patients Infected with K. pneumoniae

The antibacterial susceptibility test of a female patient urine sample containing K. pneumoniae towards the antibiotics ampicillin, gentamicin, levofloxacin and imipenem was performed as mentioned above. K. pneumoniae was found to be sensitive to levofloxacin, imipenem and gentamicin and resistant to ampicillin, as seen in FIG. 8(c). Peak intensities for levofloxacin, imipenem and gentamicin lie significantly lower compared to the control (no antibiotic) panel. On the other hand, the peak intensity of ampicillin panel coincides with the control (no antibiotic) panel suggesting that the bacteria are resistant towards that particular concentration of the ampicillin antibiotic.

Assay of Clinical Samples of Female Patients Infected with E. faecalis

The urine sample (female patient) containing E. faecalis was assayed using the method disclosed herein above for susceptibility/resistance to the antibiotics imipenem and vancomycin. The peak intensities of imipenem and vancomycin were much lower compared to the control (no antibiotics) panel suggesting that E. faecalis in the sample is sensitive to the concentrations of the antibiotics as provided in Table 1 and FIG. 8(d).

Assay of Clinical Samples of Female Patients Infected with Multi-Drug Resistant P. aeruginosa The antibacterial susceptibility/resistance of the female patient urine sample containing multi-drug resistant P. aeruginosa was tested towards the antibiotics imipenem, gentamicin and levofloxacin using the method described herein above. P. aeruginosa was found to be resistant to all the antibiotics used as interpreted by coinciding peaks for all these panels with the control (no antibiotics) panel as shown in Table 1 below and FIG. 8(e).

TABLE 1 provides the results obtained with different clinical samples; Breakpoint values as provided by EUCAST

| Antibiotic | MIC reported by Microdilution (μg/mL) | MIC reported by VITEK (μg/mL) | Concentration used for method of present invention (μg/mL) | Interpretation of results of the present method | Interpretation by VITEK | Interpretation by Microdilution |
|---|---|---|---|---|---|---|
| *Male patient urine sample infected with E. coli* | | | | | | |
| Levofloxacin | 64 | >=8 | 1 | Resistant | Resistant | Resistant |
| Imipenem | 0.25 | <=0.25 | 4 | Sensitive | Sensitive | Sensitive |
| *Female patient urine sample infected with E. coli* | | | | | | |
| Levofloxacin | 64 | >=8 | 1 | Resistant | Resistant | Resistant |
| Ampicillin | | | 8 | Sensitive | — | Sensitive |
| Nitrofurantoin | | <=32 | 64 | Sensitive | Sensitive | Sensitive |
| *Female patient urine sample infected with K. pneumoniae* | | | | | | |
| Ampicillin | 256 | >16 | 8 | Resistant | Resistant | Resistant |
| Gentamicin | 0.5 | <=1 | 4 | Sensitive | Sensitive | Sensitive |
| Levofloxacin | | | 1 | Sensitive | — | Sensitive |
| Imipenem | 0.125 | <=0.25 | 4 | Sensitive | Sensitive | Sensitive |
| *Female patient sample infected with E. faecalis* | | | | | | |
| Imipenem | 0.5 | | 8 | Sensitive | — | Sensitive |
| Vancomycin | 1 | | 4 | Sensitive | — | Sensitive |
| *Female patient sample infected with P. aeruginosa* | | | | | | |
| Gentamicin | >=32 | >=16 | 1 | Resistant | Resistant | Resistant |
| Imipenem | >=32 | >=16 | 4 | Resistant | Resistant | Resistant |
| Levofloxacin | >=32 | >=8 | 1 | Resistant | Resistant | Resistant |

Stability Test

The stability of the readouts (results) obtained from the method as disclosed herein, the following was conducted. *E. coli* sensitive to imipenem was used for the assay method as described herein above. The sample was incubated with nanoprobes in the presence of the imipenem antibiotic and the absorbance spectrum recorded every hour for duration of three hours. FIG. 9 is a graphic representation of UV-Visible spectra of the sample *E. coli* without antibiotics and with imipenem at 0 min, 1 h, 2 h and 3 h time intervals. It was observed that the spectra for the sample without antibiotics panel and imipenem panel maintained different and distinct patterns even after 3 hours, suggesting the stability of the results for 3 hours after the completion of the assay.

Determination of Minimum Inhibitory Concentration (MIC)

Based on repeated experiments, it was observed by the inventors that the concentration at which signal intensity shows 34% reduction against the control (no antibiotics) panel should be considered as MIC of the antibiotic for the causal organism. This criterion showed MIC 16 μg/ml for levofloxacin for *E. coli* which matches with the MIC obtained by CLSI reference method of microdilution. MIC determination protocol was tested on other antibiotics-bacteria combinations as well and percent reduction criterion was determined for each pair from repeated tests. The results are summarized in Table 2 below.

TABLE 2 provides the MIC determination of the present invention compared with the existing standards

| Clinical Isolate + Antibiotic | Dilution range of the antibiotic (μg/ml) | MIC obtained with the diagnostic method assay (μg/ml) | MIC Interpretation Criterion | Interpretation by diagnostic method | MIC obtained with CLSI reference method of microdilution (μg/ml) | Interpretation by CLSI reference method of microdilution |
|---|---|---|---|---|---|---|
| *E. coli* + Imipenem | 0.125-16 | 0.125 | Dilution showing 55% reduction compared to no antibiotics | Sensitive | 0.250 | Sensitive |
| *K. pneumoniae* + Levofloxacin | 1-64 | 16 | Dilution showing 34% reduction compared to no antibiotics | Resistant | 16 | Resistant |

TABLE 2-continued provides the MIC determination of the
present invention compared with the existing standards

| Clinical Isolate + Antibiotic | Dilution range of the antibiotic (µg/ml) | MIC obtained with the diagnostic method assay (µg/ml) | MIC Interpretation Criterion | Interpretation by diagnostic method | MIC obtained with CLSI reference method of microdilution (µg/ml) | Interpretation by CLSI reference method of microdilution |
|---|---|---|---|---|---|---|
| K. pneumoniae + Amikacin | 4-256 | 128 | Dilution showing 23% reduction compared to no antibiotics | Resistant | 128 | Resistant |

As seen above, for each antibiotic tested, the MIC obtained by the inventors' method closely matches the MIC obtained with CLSI reference method of microdilution. For each clinical isolate, MIC of a particular antibiotic obtained with the method as disclosed herein above is in perfect agreement with the MIC obtained from the CLSI reference method MIC. Table 2 also provides details about the MIC determination rule for each combination used which in principle can be extended to all the other bacteria-antibiotic combinations. FIG. 10 is a graphic representation of the method as disclosed herein above providing results for MIC determination for different antibiotics-clinical bacterial isolates combination.

Advantages of the Invention

The present invention provides novel diagnostic tools including diagnostic method, diagnostic system and diagnostic kit for rapid determination of antibiotic susceptibility, antibiotic resistance and minimal inhibitory concentrations of microorganisms directly in clinical samples in a rapid and reliable manner.

The present invention provides an antibiotic susceptibility testing method based on phenotypic screening of the bacteria in presence of major antibiotics being used currently, wherein the testing does not need prior culturing and works directly on the clinical samples. The present method identifies susceptibility or resistance to any number of antibiotics which are deemed to be critical or major at the time of testing.

The present invention is an advance over the routine genotypic and molecular approaches currently existing in the art that might miss the new antibiotic resistance genes or constantly evolving bacterial genomes. This is because the present invention relies on a phenotypic approach wherein the growth of the bacteria is determined and decreases room for any errors occurring in molecular approaches.

The present invention is convenient, rapid, cost-effective, has excellent selectivity and sensitivity, has the potential to significantly improve patient outcomes and helps reduce further evolution of antimicrobial resistant microorganisms.

The present invention can be employed at the point of care without the need for any extensive training, complex instrumentation, high-end infrastructural facilities, or prior culturing of clinical samples resulting in delays.

The present invention is can be performed quickly, preferably within 2 hours, which is significantly faster than the conventionally employed methods of culture that take about 48 to 72 hours to get results.

The present invention provides a rapid and reliable measure of MIC of a particular antibiotic for each clinical isolate that is in perfect agreement with the MIC obtained from the CLSI reference method MIC within the same 2 hours time required for the assay and obliterates the need for any additional time-consuming experimental assays.

The present invention can be expanded as a diagnostic platform as it provides a reliable method for testing the antibiotic susceptibility of the causal microorganism and help medical practitioners in prescribing the correct course of drugs for treatment, thus tackling the rampant misuse of antibiotics and the spread of antimicrobial drug resistance in microorganisms due to over-prescription of antibiotics.

We claim:

1. A rapid method for determining antibiotic susceptibility of a microorganism directly in a sample comprising the steps of:
   a) adding a sample to nanoprobes in the presence of an antibiotic for 30 minutes to 90 minutes at a temperature in a range of 35° C. to 37° C. along with one control set incubated under similar conditions in the absence of an antibiotic;
   b) separating the nanoprobes bound to the microorganism in the sample from the unbound nanoprobes by filtration or washing;
   c) recovering the nanoprobe-microorganism complex of step (b) using sodium acetate buffer of 10 mM having pH in a range of 4.5 to 5.5;
   d) incubating the recovered nanoprobe-microorganism complex with glucose solution of 50 to 150 mM concentration at a temperature of 37° C. for 5 minutes to 15 minutes;
   e) adding a seed solution to the solution of step (d) and allowing the solution to incubate for a period of 15 to 25 minutes; and
   f) detecting the colour change and colour intensity of the solution of step (e) at UV-Visible spectrum and comparing it with the control for determining the antibiotic susceptibility of the microorganism;
   wherein the nanoprobes are gold nanoparticles conjugated to glucose oxidase and antibodies specific against the microorganism.

2. The method as claimed in claim 1, wherein the seed solution comprises gold nanoparticles in a concentration in a range from 10 mM to 20 mM and $HAuCl_4$ solution at a concentration from 0.5 mM to 2.5 mM.

3. The method as claimed in claim 1, wherein the size of the gold nanoparticles in the nanoprobes is in a range from 15 nm to 50 nm and in the seed solution is in a range from of 2 nm to 10 nm.

4. The method as claimed in claim 1, wherein the concentration of glucose oxidase required for initiating growth of seed particles in step (e) is in a range from 10 µU/ml to 10 U/ml.

5. The method as claimed in claim 1, wherein the nanoprobes comprise antibodies of polyclonal, monoclonal or recombinant types directionally bound to the gold nanoparticles through Fc region and maintain the binding sites intact.

6. The method as claimed in claim 1 wherein the filtration is carried out using a membrane having pore size in a range from 450 nm to 200 nm diameter.

7. The method as claimed in claim 1, wherein the sample is selected from a group consisting of blood, serum, urine, saliva, nasal discharge, sweat, plasma, semen, cerebrospinal fluid, tears, pus, amniotic fluid, lung aspirate, gastrointestinal contents, vaginal discharge, urethral discharge, chorionic villi specimens, epithelials, hair, and sputum.

8. The method as claimed in claim 1, wherein the antibiotic is selected from a group consisting of Amikacin, Amoxicilin-Clavulanate, Ampicillin, Aztreonam, Benzylpenicillin, Cefazolin, Cefepime, Cefoxitin, Cefixime, Ceftazidime, Cefoperazone-Sulfobactam, Ceftriaxone, Cefotaxime, Cephalexin, Chloramphenicol, Ciprofloxacin, Cefuroxime, Colistin, Ertapenem, Erythromycin, Fosfomycin w/G6P, Gentamicin, Imipenem, Doxycycline, Daptomycin, Colistin, Levofloxacin, Linezolid, Nitrofurantoin, Norfloxacin, Oxacillin, Meropenem, Minocycline, Piperacillin-Tazobactam, Tigecycline, Tobramycin, Trimethoprim, Trimethoprim-Sulfomethoxazole, Teicoplanin, Tetracycline, and Vancomycin.

9. The method as claimed in claim 1, wherein the microorganism is bacteria, fungi, or parasite.

10. The method as claimed in claim 1, wherein the microorganism is gram positive bacteria, gram negative bacteria, or Myxobacteria.

11. The method as claimed in claim 1, wherein the microorganism is gram positive bacteria selected from *Staphylococcus, Enterococcus, Streptococcus, Corynebacterium, Listeria, Bacillus, Nocardia, Clostridium,* and *Actinomyces*.

12. The method as claimed in claim 1, wherein the microorganism is gram negative bacteria selected from *E. coli, Enterobacter, Salmonella, Shigella, Proteus, Citrobacter, Pseudomonas, Burkholderia, Stenotrophomonas, Acinetobacter, Vibrio, Yersinia, Legionella, Haemophilus, Bordetella, Brucella, Bartonella, Campylobacter, Bacteroides, Fusobacterium, Porphyromonas, Prevotella, Neisseria, Moraxella,* and *Veillonella*.

13. The method as claimed in claim 1, wherein the microorganism is *Mycobacterium* having species *M. tuberculosis,* and *M. avium-intracellulare*.

14. The method as claimed in claim 1, wherein the detection of step (f) can be carried out at a single wavelength of 545 nm.

15. The method as claimed in claim 1, wherein the change in colour of the solution of step (e) upon incubation from colourless to red indicates the presence of seed particle growth and the increasing gradation of colour intensity is directly correlated to the increasing resistance of the microorganism to the antibiotic used in the method.

16. The method as claimed in claim 1, wherein the time taken for determination of antibiotic susceptibility in a microorganism directly in a sample is in a range of 2 hours to 4 hours.

17. The method as claimed in claim 1, wherein minimal inhibitory concentration (MIC) value of an antibiotic for a microorganism is determined within 2 hours to 4 hours.

18. A diagnostic system for rapid determination of antibiotic susceptibility in microorganisms comprising:
    (a) a cassette comprising at least one or more antibiotic well comprising an antibiotic and nanoprobes, and one control well devoid of any antibiotic; and
    (b) an analyzer for spectral determination and display of the results;
    wherein the nanoprobes are gold nanoparticles conjugated to glucose oxidase and antibodies specific against the microorganism.

19. The system as claimed in claim 18, wherein the size of the gold nanoparticles in the nanoprobes is in a range of 15 nm to 50 nm.

20. The system as claimed in claim 18, wherein the nanoprobes have antibodies directionally bound to the gold nanoparticles through Fc region for maintaining the binding sites intact.

21. The system as claimed in claim 18, wherein the wells of the cassette comprise culture media for promoting growth of the microorganism.

22. The system as claimed in claim 18 or 21, wherein the antibiotic, nanoprobes and culture media are present in lyophilized form in the wells.

23. The system as claimed in claim 18, wherein more than one cassette can be housed for simultaneous run of more than one clinical sample.

24. The system as claimed in claim 18, wherein the cassettes are disposable and can be discarded after each run.

25. The system as claimed in claim 18, wherein the analyzer detects and analyses the results under UV-visible absorption spectrum or at a fixed wavelength of 545 nm or both.

26. A kit for rapid determination of antibiotic susceptibility of a microorganism comprising:
    a) one or more nanoprobes;
    b) one or more antibiotics;
    c) buffer component having pH 4.5 to 5.5;
    d) seed solution;
    e) glucose solution of 50 mM to 150 mM;
    f) one or more capillary tubes for transfer of sample;
    g) one or more single use tubes for carrying out the assay;
    h) one or more filtration devices; and
    i) reading material comprising directions for use and comprehending the results for determination of antibiotic susceptibility of the microorganism in the sample;
    where in the nanoprobes are gold nanoparticles conjugated to glucose oxidase and antibodies against one or more microorganism; and
    where in the antibodies are directionally bound to the gold nanoparticles through Fc region and maintain the binding sites intact.

27. The kit as claimed in claim 26, wherein the seed solution comprises gold nanoparticles at a concentration in a range from 10 nM to 20 nM and $HAuCl_4$ solution at a concentration in the range from 0.5 mM to 2.5 mM.

28. The kit as claimed in claim 26, wherein the size of the gold nanoparticles in the nanoprobes is in a range of 15 nm to 50 nm and in the seed solution is in a size range from 2 nm to 10 nm.

* * * * *